United States Patent [19]
Miller et al.

[11] Patent Number: 5,624,810
[45] Date of Patent: Apr. 29, 1997

[54] METHOD FOR DETECTION OF SURFACES CONTAMINANTS

[75] Inventors: C. David Miller, Greenbelt; Lawrence Loomis, Columbia, both of Md.

[73] Assignee: New Horizons Diagnostics Corp., Columbia, Md.

[21] Appl. No.: 370,093

[22] Filed: Jan. 9, 1995

[51] Int. Cl.$^6$ .................................................. C12Q 1/66
[52] U.S. Cl. ........................... 435/8; 435/29; 435/968; 436/1; 436/172
[58] Field of Search .............................. 435/29, 968, 8, 435/299, 311, 296, 292; 436/1, 172, 800

[56] References Cited

U.S. PATENT DOCUMENTS

| | | | |
|---|---|---|---|
| 4,385,113 | 5/1983 | Frosch et al. | 435/8 |
| 4,598,044 | 7/1986 | Kricka et al. | 435/8 |
| 4,978,504 | 12/1990 | Nason | 435/296 |
| 5,366,867 | 11/1994 | Kawakami et al. | 435/8 |

Primary Examiner—Leslie Wong

[57] ABSTRACT

A method for determining the presence and concentration of total microbial contamination or the presence and concentration of a specific microbial species on a surface is described. The method consists of a means of a collection device and fluid for removing the microbes from the surface and suspending them in a fluid phase. An aliquot of the fluid phase is introduced into a disposable test device which allows filtration of the sample to remove extraneous substances including somatic cells, and concentration of the microbes. The total concentration of microbes is determined by adding a bacterial releasing reagent and a luminescent reagent to the disposable test device and introducing the disposable test device into a luminometer that can read the luminescence from the side wall. The presence and concentration of specific microbial species is determined by adding an aliquot of the fluid phase described above to the dispoable test device, washing the sample, then adding a specific labeled antibody directed against the microbes to be detected to the test device, washing then adding a luminescent reagent to the disposable test device. The test device is then introduced into the luminometer. The relative light units determine the presence and quanity of microbes present. In both cases, the microbe is identified and/or the concentration is determined in less than 1 hour and generally in less than 5 minutes.

30 Claims, 3 Drawing Sheets

METHOD FOR DETECTION OF SURFACES CONTAMINANTS

FIELD OF THE INVENTION

The present invention relates to a method for detecting the presence and determining the quantity of contaminants on surfaces. More particularly, the invention relates to a method for rapidly determining the total microbial contamination or for determining the presence and quantity of specific microbial or chemical contaminant present on a wide variety of surfaces including surfaces of meat carcasses or other food, surfaces of equipment, surfaces where food is being processed or prepared, and surfaces of equipment, gloves and materials in medical situations. Furthermore, the invention relates to a method for determining the total microbial or specific microbial or chemical contamination by bioluminescence or chemiluminescence.

BACKGROUND OF THE INVENTION

Microbial contamination of surfaces is a significant cause of morbidity and mortality. Rapid and routine procedures for quantitative determination of bacteria present on surfaces is frequently of vital importance, particularly in food processing and in hospitals. Food poisoning is often a result of microbial contamination of meat or food that occurs during processing. Contamination can be spread through contact of food with surfaces. In addition, spread of disease in hospitals and other facilities often occurs as a result of passage of infectious microbes on the surface of clothes or equipment.

Key feature of these applications is the requirement for rapid testing within minutes, a method that will overcome the potential contaminants from a variety of surfaces, a requirement for no cross-over in the results from one test to a second, and a need for both general and specific testing for microbes, that is, the ability to test for contamination by both total microbial counts and the ability to test for the presence of specific microbes.

Various methods have been utilized to measure microbial contamination on surfaces. Traditional procedures for assaying bacteria on surfaces are based on swabbing the surface followed by a culture of the swab for 24 to 48 hours in or on media that supports the growth of microbial species. The cultures are observed manually or with automated instrumentation to determine the number of colonies that have formed as an indicator of the number of microbes initially present on the surface. The disadvantages of this methodology are long assay times, requirements for specially trained personnel, and possible inadequate identification of the presence of certain potentially pathogenic microbes whose growth is not supported by the specific media or environment. In particular, it may be difficult to detect fungal contamination by this method. In addition, in many of the potential applications, the method does not give results in the time frame required for effective response.

Luminescent reactions have been utilized in various forms to detect bacteria in fluids and in processed materials. In particular, bioluminescent reactions based on the reaction of adenosine triphosphate (ATP) with luciferin in the presence of the enzyme luciferase to produce light, the "firefly" reaction have been utilized. Since ATP is present in all living cells including all microbial cells, this method can be used in a rapid assay to obtain a quantitative estimate of the number of living cells in a sample. Early discourses on the nature of the reaction, the history of its discovery, and its general area of applicability are provided by E. N. Harvey (1957), A History of Luminescence: From the Earliest Times Until 1900, Amer. Phil. Soc., Philadelphia Pa. and W. D. McElroy and B. L. Strehler (1949) Arch. Biochem.Biophys. 22:420–433. Alternatively, chemiluminescent detection by isoluminol or similar compounds has been used. This method is based on the detection of iron-containing substances in microbes.

Test procedures exemplifying the use of bioluminescent reactions for bacterial determinations and, specialized instrumentation for measurement of the associated light emission, are known and have been disclosed. Plakas (U.S. Pat. Nos. 4,013,418, 4,144,134, and 4,283,490) teaches a bioluminescent assay for the detection of bacteria in a sample including the steps of lysing non-bacterial cells, effecting filtration by positive pressure, washing, lysing bacterial cells and detecting ATP released with a luciferin/luciferase/Mg2+ reagent. This art in this patent does not deal with the specific problems associated with collection of material from a surface or with the detection of specific bacteria. No issue of the timing is mentioned and the invention as disclosed would require significant time.

Chappelle in U.S. Pat. No. 4,385,113 discloses a method for detection of bacteria in water based on bioluminescence. This test requires several hours to perform and is specifically addressed to the detection of total bacterial content in water.

Miller (PCT application US88/00852) discusses a similar assay for use with urine samples, but does not discuss the issues of collection from a surface and the assay timing is not specifically set forward in this application. Further, no method for detection of specific bacteria is elucidated.

Clendenning in his U.S. Pat. No. 3,933,592 discusses a method for bioluminescent detection of microbial contamination and in the examples refers to performing the procedure in less than 2 minutes. The procedure does not involve pre-treatment phases and the removal of somatic cell ATP.

AEgidius (U.S. Pat. No. 5,258,285) discloses a method for detection of bacterial concentration in a sample that utilizes a filtration step, a washing step to remove extraneous material including somatic cell ATP, establishing an extraction chamber in which the bacterial ATP is extracted, then transferring the material to a measuring chamber in which luciferin/luciferase/Mg2+ is added and the reaction measured. This method does not mention time. In addition, it utilizes separate chambers for washing, extracting the bacterial ATP, and measuring the reaction. This may potentially result in decreased sensitivity due to loss of the material in the process of transferring the solution from chamber to chamber. Further, the method does not describe a means of collecting a sample from a surface.

Detection of bacteria on surfaces poses additional issues not addressed in these previous methods. First and foremost is the method for collecting a sample to be compatible with these test devices and materials. The method must effectively retrieve the bacteria from the surface and result in a liquid suspension of the microbes.

A second issue of main concern is that surfaces being monitored often are contaminated with materials that may interfere with the detection of the microbes. One main interfering material that can be present on surfaces is somatic cells either from the food itself and including both animal and plant cells, or from the hands of an individual in contact with the surface. Since all living organisms including somatic cells contain ATP, the presence of these cells can mask or alter the reading obtained.

An additional source of interfering substances are those that interfere with the light producing reaction itself. These substances include a wide range of chemicals such as chlorine, oxidizing agents, free ATP, heavy metals, and other chemicals. As some of these chemicals are used for disinfecting of a surface, it is obvious that a reliable method for analyzing microbial contamination must include a means of eliminating these substances from the sample.

It is a further requirement in many cases in the food processing and hospital applications that the method for monitoring for microbial contamination of surfaces be rapid. For example, in the processing of beef carcasses, the carcasses are processed on a line and any testing of the material for microbial contamination must be performed within the time frame required for the carcass to move to further processing.

Previously disclosed luminescence based methodologies for microbial detection have not included any means for processing a sample from a surface and making a liquid suspension for testing. Further, the processes have required multiple devices or chambers for containment, filtration, and measurement of the reaction. Finally, the processes have not incorporated a disposable device that allows for minimizing cross-contaminations. Finally, in those assays for detecting specifically microbial ATP and other specific surface contaminants, previously disclosed inventions have relatively long time frames which are not consistent with on-line processing, quality control, and immediate verification of results.

SUMMARY OF THE INVENTION

The present invention is a method and device for determining the presence and/or concentration of total microbial concentration or the presence and/or concentration of a specific target analyte derived from a surface. The method firstly comprises collecting a surface sample by wiping a circumscribed area of a surface in a prescribed fashion using a collection apparatus means comprised of an absorbent or adsorbent material. The said collection apparatus means is placed into a container containing a fluid and agitated to release the surface contaminants from the collection apparatus means into the fluid. The collection apparatus means can be in the form of a sponge or a swab and the container can be a bag, tube, or small cup. An aliquot of the fluid phase is subsequently transferred to a disposable test device comprised of a translucent hollow cylinder, open on the top and having a porous filter attached on the bottom. The fluid phase is filtered through the disposable test device by applying either positive or negative pressure resulting in retention of microbes or target analytes on the surface of the filter. The filtration process results in the concentration of analyte and the removal of any interfering substances from the collectate prior to testing, such as inhibitors or any nonspecific materials to maximize test sensitivity and specificity. The filter retentate can be washed by adding appropriate wash solutions and reapplying appropriate pressure to three the fluid phase through the filter. Another feature of the present invention is that the retentate captured on the filter of the disposable test device can be assayed by a chemiluminescent or bioluminescent test method. Said final step of said test method comprising addition of a luminescent substrate to the retentate resulting in a chemiluminescent reaction and measuring the light output from said chemiluminescent reaction by using a photometer that accommodates the disposable device in a manner which allows its precise and reproducible positioning with respect to the surface of the photosensor and which precludes any possible loss of the final reaction mixture during and after the measurement cycle.

The present invention allows for a surface contaminant to be identified and/or concentration determined in less than 1 hour from time of collection to end result, and generally in less than 5 minutes.

More specifically, the present invention comprises a method for performing chemiluminescent assays such as bioluminescent assays for ATP, chemiluminescent immunoassay or DNA probe assays. One embodiment of the present invention is a method for determining the total microbial contamination comprising the steps of:

a) collecting a surface sample with a collection apparatus means and b) agitating said collection apparatus means with a fluid phase to dislodge the surface contaminants into a fluid phase, said fluid phase the becoming the collectate and c) placing an aliquot of said collectate into a disposable test device, and d) adding a washing/lysing reagent that lyses any somatic cells present in the aliquot and e) applying positive pressure to the top of the disposable test device or negative pressure to the bottom of the disposable test device to eliminate the liquid phase containing free ATP and any chemical inhibitors as well as concentrating the bacteria at the interface, and f) adding a bacterial lysing reagent that perforates the bacterial cell walls allowing the release of microbial ATP, and g) adding ATP free luciferin and luciferase reagent, and h) determining the amount of ATP present by measuring the light emitted through translucent sides of said disposable test device.

The choice of collection fluids are well known to those skilled in the art. Generally the fluid is comprised of a detergent, salt, or buffer or any combination thereof that maintains the integrity of the microbial cell walls. A fluid consisting of 0.15M sodium chloride containing 0.5% Tween 20 detergent is one such choice. It is possible to use other formulations including phosphate or HEPES buffered saline and other detergents including zwitterionic detergents and non-ionic detergents.

It will be obvious to a person skilled in the art that mixing of reactant could be achieved in any of the steps through the use of a micropipette. The detection method of this invention specifically allows for both the concentration of analyte and any resulting chemiluminescent reaction caused by the presence of said analyte to occur within the chamber of the disposable test device. An added feature of the disposable test device is that the diameter of the filter is from 0.5 to 2.0 cm, preferably about 1.0 cm, so that the volume of bioluminescent or chemiluminescent substrate solution is minimized to maximize signal output to the photodetector means. The final volume of the substrate should be between 20 µl to 1000 µl, most preferably about 60 µl to 100 µl. The disposable test device can be inserted into a complementary device comprising a larger (liquid tight) at least two component chamber that can house the disposable test device and through which a volume of collectate greater than 500 µl can pass through the filter under positive or negative pressure and retain the microbes or the analytes of interest onto the surface of the filter. For example, the disposable test device can be inserted into the lower chamber of the two component device, said lower chamber having an outflow for the filtrate to which is attached a removable upper chamber of the two component device. The said upper chamber comprising a liquid tight seal to said lower compartment and having an intake valve. Said intake valve can be configured for a complementary luer tip fitting for attachment of a luer tipped syringe. Said syringe may include at least one series of prefilter(s) to remove any larger debris from entering the filter of the disposable test device. At completion of passing the collectate through the filter of the disposable test device, the two component device can be opened, and the disposable test device physically removed. Said disposable test device now containing the retentate from a large volume of collectate (i.e. 50 ml). The filtration of said large volume of collectate enables increased sensitivity for analyte detection of the collectate fluid. Said disposable test device is then processed as previously described.

The luciferin/luciferase chemiluminescent reactions for ATP are well known. Other chemiluminescent reactions employing bacterial luciferase reactions, or luminols for total microbial determinations can be easily adapted to the methods and devices of the present invention.

The invention further concerns a detection method in which the presence and quantity of specific microbes on a surface can be detected in a time frame less than one hour, said method comprising the steps of:

a) Providing a clean disposable test device comprising an open top, translucent sides, and a porous filter attached to the bottom side, b) Adding an aliquot of collectate, said collectate being that described as above, c) Adding an appropriate wash solution comprised of detergent, or buffered salts or a combination thereof, d) Applying positive pressure to the top of the disposable test device, or negative pressure to the bottom of the disposable test device to remove fluid from the device and deposit microbes or target analytes directly or indirectly onto the surface of the porous filter, e) Adding a specific labeled antibody directed against the specific microbes to be detected and incubating for an appropriate period of time, f) Applying positive pressure to the top of the disposable test device, or negative pressure to the bottom of the disposable test device to remove fluid containing unreacted enzyme labeled antibody from the device, g) Adding an appropriate wash solution comprised of detergent and buffered salts, h) applying positive pressure to the top of the disposable test device, or negative pressure to the bottom of the disposable test device to further remove fluid containing unreacted labeled antibody from the device, i) Adding a chemiluminescent substrate and determining the amount of light emitted by the chemiluminescent substrate using a photometer that accommodates the disposable test device in a manner which allows its precise positioning with respect to the surface of the photosensor and which precludes any possible loss of the final reaction mixture during and after the measurement cycle.

The method described above can also be modified by adding capture particles such as latex spheres coated with a binder such as specific antibody to antigens of the target microbe into the disposable test device prior to performing step (d). The method can also be modified so that capture particles and enzyme labeled antibody and the collectate are all simultaneously reacted within the disposable test device, prior to performing step (f).

Various buffers for extracting antigens and washing immune complexes are well known to those skilled in the art.

DETAILED DESCRIPTION OF THE PREFERRED EMBODIMENT

In the following description, the various forms of the method of the invention and the uses of the various forms of the apparatus therein will be described in exemplary terms only, as a general bacterial screen and as a specific test for Salmonella. This discussion, however, is simply to illustrate the steps of the method and the structure and use of the devices and apparatus therein. The best modes, as described hereinafter, are accordingly, to be considered exemplary and not limiting as to the scope and concept of the invention.

Figure 1:
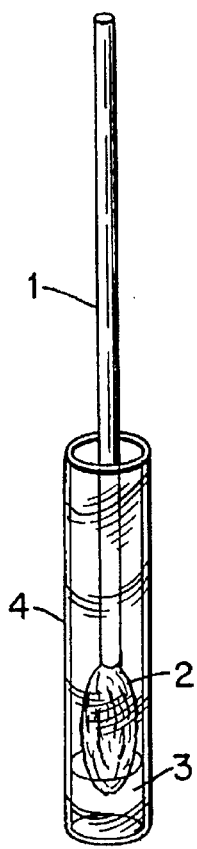
FIG. 1 is a drawing of the collection apparatus means comprising a shaft, absorbent tip, and a container with fluid.

One aspect of the invention is the collection device. FIG. 1 is a drawing of a collection apparatus means comprised of a shaft (1) and absorbent tip (2). The absorbent tip is wetted with an excess of collection fluid (3) and used to wipe a circumscribed area of a surface to be monitored. After wiping the area, the absorbent tip is place into a container (4) and agitated to release any of the absorbed bacteria into the collection fluid.

Figure 2:
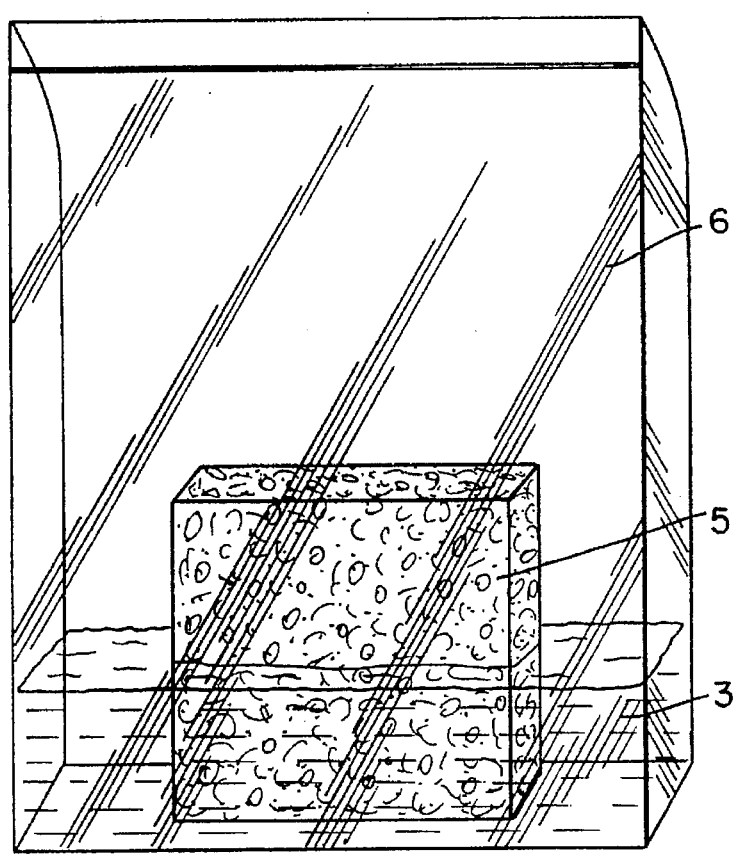
FIG. 2 is a drawing of the collection apparatus means comprising a sponge and a bag with fluid.

Referring to FIG. 2 is a drawing of a collection apparatus means comprised of a sponge. The sponge (5) is wetted with collection fluid (3) and used to wipe a circumscribed area of a surface to be monitored. After wiping the area, the sponge is placed into a plastic bag (6) containing excess collection fluid and squeezed several times to release any of the absorbed bacteria into the collection fluid. The volume of collectate fluid can vary depending upon the size of the absorbent and area wiped. The collection fluid is selected to ensure transfer of the microbial contaminants from the test surface to the collection device and then to a disposable test device. Generally the pH of the collection fluid is between 5 and 8, but preferably between 6.0 to 7.0 and contains salts such as sodium chloride between 0.1M and 0.3M, preferably about 0.25M NaCl to ensure survival of bacteria. The collection fluid should contain a detergent such as 0.05% tween 20 to ensure that the bacteria are easily removed from the test surface and collection apparatus.

Figure 3:
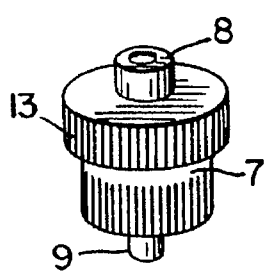
FIG. 3 is a drawing of a large volume concentrating apparatus.

Referring to FIG. 3 is a drawing of a large volume concentrating apparatus (7), in which a quantity of collectate fluid can be collected into a disposable test device. An appropriate sized luer-tipped syringe is attached to the inlet (8) of large volume concentrating apparatus and then positive pressure applied to the syringe plunger causing the collectate fluid to flow out of the outlet (9).

Figure 4:
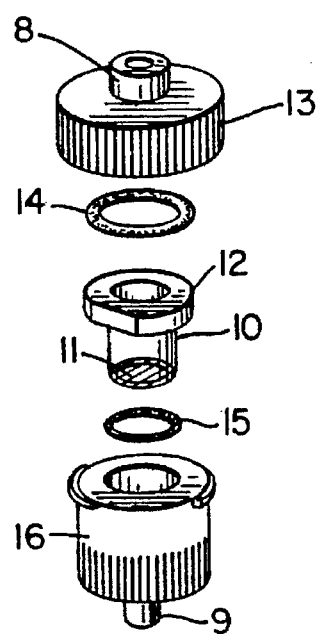
FIG. 4 is an exploded perspective view of a large volume concentrating apparatus.

Referring to FIG. 4 is an exploded perspective view of the large volume concentrating apparatus, the collectate fluid flows through the filter bottom (11) of the disposable test device (10). O rings (14) and (15) provide a leakproof seal. After completion of concentrating the collectate, upper compartment (13) is separated from the lower compartment (16) to expose the lip (12) of the disposable test device. The disposable test device is then manually removed from the lower compartment.

Figure 5:
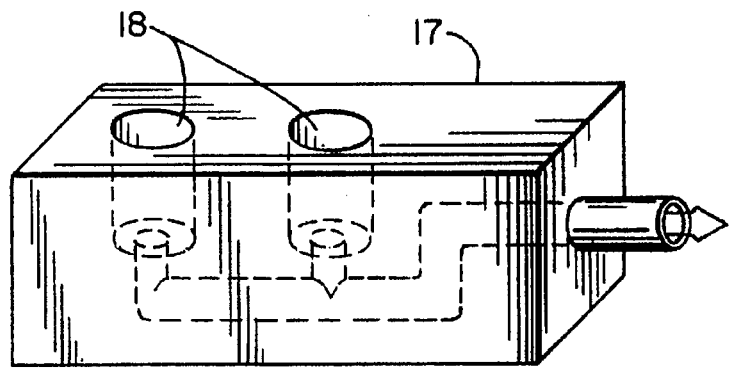
FIG. 5 is a drawing of a negative pressure apparatus.

Referring to FIG. 5 is a negative pressure device (17) in which the bottom portion of the disposable test device is inserted into holes (18). Appropriate volume of wash or somatic cell lysing solutions can be added and a vacuum can be applied to outlet (19) to remove fluid from the disposable test device.

Figure 6:
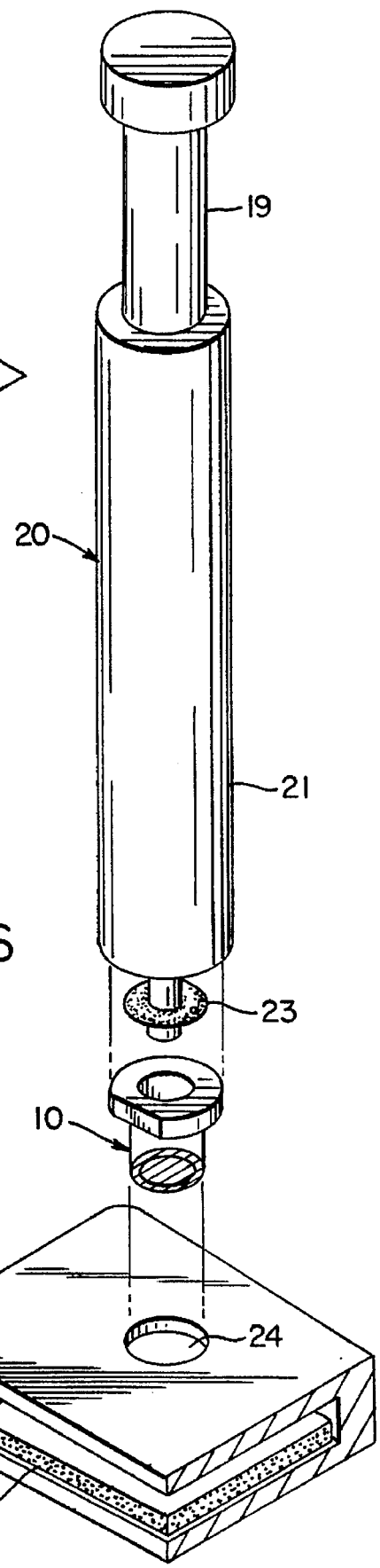
FIG. 6 is an exploded perspective drawing of a positive pressure apparatus, disposable test device and holder with absorbent pad.

Referring to FIG. 6 is an expanded perspective drawing of a positive pressure apparatus (20) comprised of a plunger (19) and a barrel (21), a disposable test device (10), and device holder (25) comprised of an absorbent pad (26) to absorb the fluid waste. The disposable test device is inserted into holder (24). An aliquot of collectate fluid (i.e. 50 to 100 µl) is added and an appropriate volume of wash or somatic cell lysing solutions can be added. The rubber seal (23) of the positive pressure device is positioned on top of the disposable test device. Applying pressure to plunger (19) forces air through barrel (20) and out through outlet (22) displacing the fluid which passes into the absorbent pad. Additional wash solution can be added and the process repeated.

Figure 7:
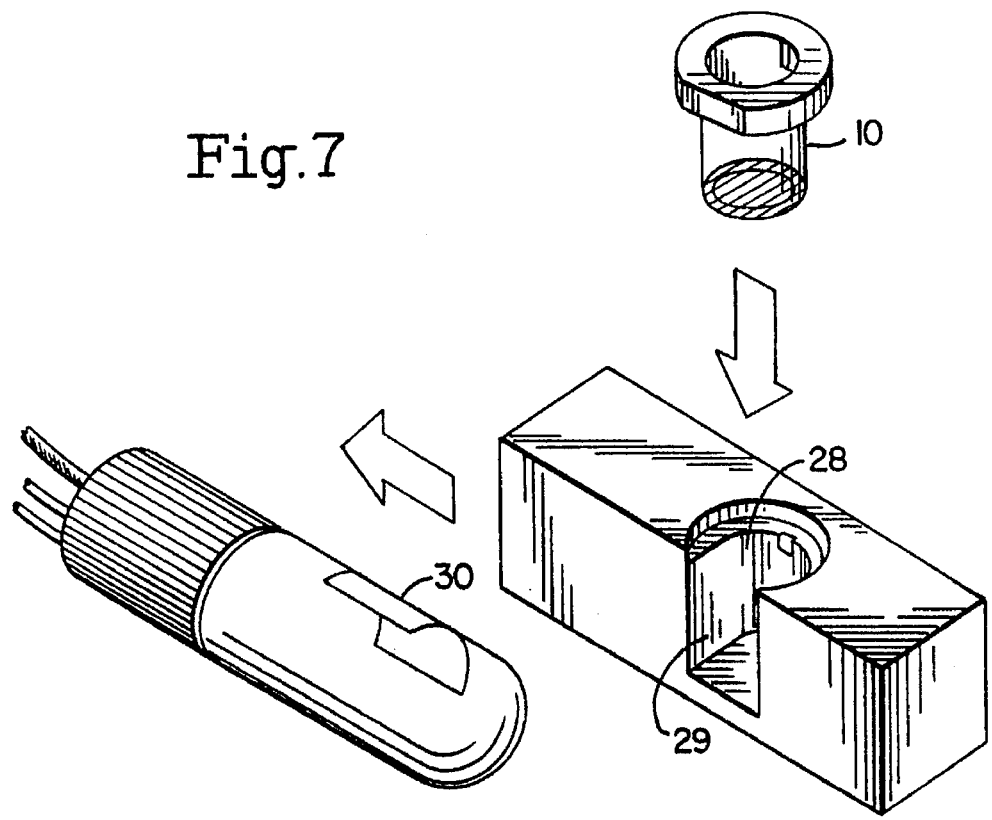
FIG. 7 is a drawing of the disposable test device, its respective positioning into the complementary draw slide and the relationship to the photosensor means.

Referring to FIG. 7 is a drawing of the disposable test device (10), its respective positioning (28) into the draw slide (27), and the relationship to the photosensor means (30). The body of the disposable test device (10) is comprised of optically clear molded plastic material, such as polystyrene, which is capable of nearly complete transmission of light within a 500–600 nm wavelength range. Fused to the lower surface of the device is a semi-permeable membrane (11) which is characterized by its strength and lack of deformation under pressure, and a pore size distribution which insures surface retention of bacterial cells, while facilitating complete passage of any associated liquid phase during pressurization. This membrane must also have sufficient surface tension to retain the measurement solution even after wetting.

The draw slide is an integral part of a luminometer instrument. The draw slide is pulled out and the disposable test device is positioned into hole (28) so that a window to the translucent wall of the disposable test device is exposed to the photosensor means when the draws slide is returned to a complementary dark chamber of the luminometer.

In a general bacterial screen based on bioluminescence, after a microbial sample has been concentrated in the disposable test device, a bacteriolytic reagent is added to lyse the bacteria and free the ATP. An appropriate volume of luminescent substrate (i.e. luciferin-luciferase) is added to the disposable test device and the draw slide is returned to the dark chamber of the luminometer. Measurement of light emission is made by digitalizing or converting the electrical signal from the photosensor means to a number of relative light units. If the method is to be used to detect specific bacteria, a specific antibody conjugated to a chemiluminescent or enzyme probe is added. In the preferred embodiment, the antibody is placed in the disposable test device and allowed to react for 10 minutes. Additional wash steps may be performed by adding a wash solution and evacuating the wash solution. A luminescent substrate solution is then added. In the preferred embodiment such substrate consists of a mixture of hydrogen peroxide and luminol. The draw slide is returned to the dark chamber of the luminometer. Measurement of light emission is made by digitalizing or convening the electrical signal from the photosensor means to a number of relative light units.

The invention is further illustrated by means of the following examples.

EXAMPLE 1

General Bacterial Screen on Hard Surfaces

This example involves a procedure for testing a stainless steel surface for the presence of microbial contamination.

*Escherichi coli* were grown on tryptic soy agar for 18 hours at 30° C. A sample of the bacteria was introduced into 10 mls of peptic soy broth and incubated for an additional 18 hours. Bacteria were harvested by centrifugation and washed three times in 0.9% NaCl that had been sterile filtered. The optical density of the solution was measured at 650 nm and the concentration was adjusted so that the optical density was 0.300. Three serial 10-fold dilutions were prepared to arrive at a concentration of $10^5$ microbes/ml. 100 µl of this solution was dribbled over an area of 10×10 cm demarcated on the surface or a stainless steel sheet that had been previously cleaned with bleach, alcohol and sterile distilled water. The solution containing the bacteria was allowed to dry for 5 hours at room temperature. Control demarcated areas were prepared with no bacteria.

Individual sponges of 10×10 mm were premoistened with approximately 750 µl of a collection fluid comprised of 0.15M NaCl containing 0.05% Tween 20 in a bag. This solution was just sufficient to completely wet the sponge. Each sponges was removed from a bag and wiped over demarcated areas of the surface with 10 strokes in each direction. The sponge was then returned to the bag and squeezed manually ten times yielding a collectate. An aliquot (25 µl) of the collectate was removed from the bag and placed in a disposable test device. 25 µl of bacterial releasing reagent was added and 50 µl of a luciferin/luciferase/magnesium mixture was added. The draw slide was closed and the relative light units determined.

In a second set of experiments, swabs were premoistened with approximately 300 µl of collection fluid in a bag as outlined above. The swabs were used to wipe similarly demarcated areas of a stainless steel surface as described above.

In each case, control areas which had not had bacteria seeded on the surface were also tested. In addition, the bacterial solution that had been seeded onto the surface was placed directly into the collection fluid as a positive control. Each data point represents the average of three samplings. Referring to Table 1, approximately 80% of seeded bacteria could be detected using either a sponge or a swab as a collection means.

TABLE 1

| Collection Device | Negative Control Surface (Relative Light Units) | Positive Control Direct Seeding (Relative Light Units) | Sample from Seeded Surface (Relative Light Units) | % Recovery of Seeded Bacteria |
| --- | --- | --- | --- | --- |
| Sponge | 0 | 115 | 88 | 79% |
| Swab | 0 | 330 | 272 | 82% |

EXAMPLE 2

General Bacterial Screen on Carcasses

This example involves a procedure for testing the surface of beef, pork, and poultry carcasses in a slaughterhouses for the presence of microbial contamination.

Testing of beef carcasses was performed in the slaughterhouse environment. Carcasses were sampled immediately before washing (alter trimming) and after the final wash. A test area on the carcass was sectioned off with either a stainless steel template defining an area of 500 cm2 or an area of that size was marked with edible ink. Random sites on the carcass were chosen for sampling.

Samples were taken with disposable sponges prepackaged in sterile bags. The sponges were premoistened by incubation with 25 ml of collection solution containing 0.085% NaCl with 0.05% Tween 20, pH 7.2. Before sampling, the excess collection fluid is mechanically expressed from the sponge. The marked area was sampled by wiping the sponge over the area approximately 15 times in both the horizontal and the vertical directions. The sponge was returned to the bag and mechanically agitated using a stomacher apparatus for two minutes.

50 µl of the sample was removed from the collection fluid and added to a disposable test device. 100 µl of wash solution comprising 0.05% saponin in 0.1M Hepes buffer, pH 7.75 was added. Using a positive pressure device, the fluid phase in the disposable test device was passed through the membrane onto a pad of paper towels. An additional 150 µl of wash solution was added and using positive pressure was passed through the membrane of the device onto a pad of paper towels. The disposable test device was placed into the drawslide of a luminometer and 30 µl of bacterial releasing reagent consisting of 0.1M benzyal konium chloride in Hepes buffer, pH 7.75 were added followed by addition of 30 µl of luciferin/luciferase/magnesium solution. The draw slide of the luminometer was closed and the light emission was read. The entire procedure required under 5 minutes to perform per sample. The results were expressed in relative light units. An aliquot of the collectate was also treated in the conventional manner of streaking the material on tryptic soy agar plates and incubating the plates for 40 hours at 30° C. after which total plate counts were determined by an automated colony plate counter.

Figure 8:
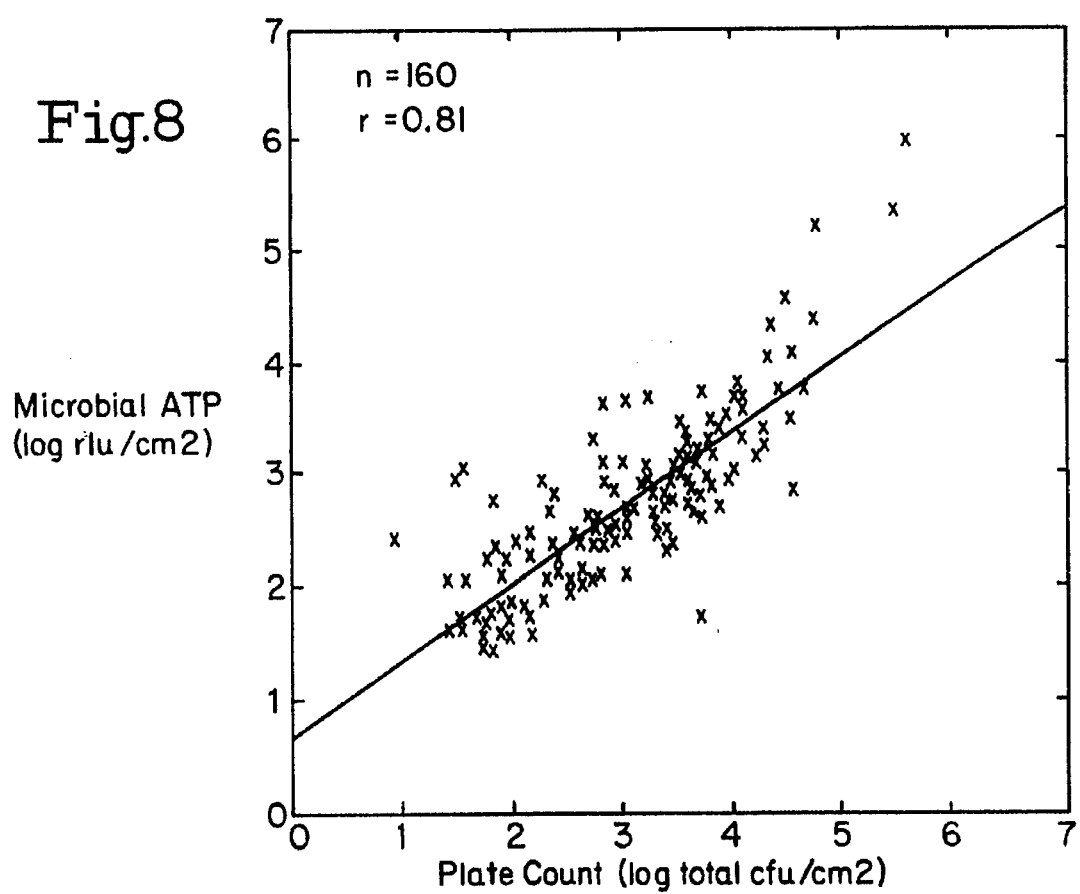
FIG. 8 shows the comparison of the total plate count obtained after 48 hours of incubation and the relative light units obtained from the 5 minutes bioluminescent procedure outlined in the preferred embodiment. Each data point was from a single beef carcass.

FIG. 8 shows the relative correlation between the plate counts determined by an automated plate counter compared with the relative light units for samples from 160 carcasses sampled at two sites. Each value is expressed as its arithmetic log. Similar data was collected for 400 carcasses at each of two sites. For this data, the correlation coefficient between the log of the relative light units (log mATP) and the log of the aerobic plate counts (log APC) was 0.92.

Similar in-plant studies were performed on 320 pork carcasses taken in three commercial plants. The correlation coefficient between log mATP and log APC was 0.92.

Comparative mATP and APC data were obtained on 330 poultry samples from two commercial poultry plants at four locations in the plant: post-pick, post evisceration, post-final wash, and post chill. The correlation between log mATP and log APC was 0.85.

EXAMPLE 3

Chemiluminescent Salmonella Assays

This example involves a procedure for testing for the presence of salmonella.

Bacteria, either *Salmonella typhimurium*, ATCC 14028 or *Aeromonas hydrophila*, ATCC 7966, were streaked from frozen stocks onto tryptic soy agar plates and incubated for 18 hours at 26° C. Bacterial colonies were harvested into sterile 0.9% NaCl and washed three times by centrifugation and resuspension in 0.9% NaCl. The optical density of the solution was measured at 650 nm and the concentration was adjusted so that the optical density was 0.300 by diluting the bacteria in 0.05M Tris, 0.05M EDTA, 0.15M NaCl, pH 8.2.

An aliquot (10 µl) of a 0.5% solution of latex microspheres coated with antibody to salmonella was added to the disposable test device. An aliquot, 100 µl, of the diluted bacteria were placed in a disposable test device with a filter on the bottom surface composed of 1.2 micron Biodyne C. After the aliquot of the bacteria was added the solution was allowed to sit for 10 minutes.

Positive pressure was applied and the fluid was evacuated onto an absorbent pad. The trapped antigens were washed by adding 200 µl of wash solution consisting of 0.01M PBS, pH 7.2 containing 0.05% Tween 20. Positive pressure was again applied and the fluid was evacuated onto an absorbent pad. A horseradisch peroxidase labeled antibody directed against Salmonella was added to the disposable test device and allowed to sit for 10 minutes at room temperature. Positive pressure was again applied and the fluid evacuated from the disposable test device. A wash solution was added and evacuated with positive pressure two more times. The disposable test device was placed in a luminometer. 100 µl of Lumiglo Chemiluminescent substrate (Kirkegaard and Perry Laboratory, Gaithersburg, Md.) was added, the drawer slide was immediately closed and the light emission determined.

The results shown in Table 2 indicate that the concentrations as low as $10^5$ organisms could be easily distinquished from a negative control using this system.

TABLE 2

Results of a Test for Salmonella

| Total Number of Organisms | Relative Light Units for *Salmonella typhimurium* | Relative Light Units for *Aeromonas hydrophila* | Signal to Noise Ratio |
|---|---|---|---|
| $10^8$ | 18,940 | 5,290 | 3.6 |
| $10^7$ | 13,780 | | 2.6 |
| $10^6$ | 10,720 | | 2.0 |
| $10^5$ | 9,220 | | 1.7 |

A second procedure was used similar to that detailed above, except that no latex beads were added to the disposable test device prior to the introduction of the aliquot of the bacteria. In this case, the signal to noise ratio for a solution of *S. typhimurium* ($10^8$ organisms): *A. hydrophila* ($10^8$ organisms) was 5.91.

A third procedure was also tested. In this method, 40 µl of latex microspheres coated with antbody to salmonella, 40 µl of sample, and 40 µl of horseradish peroxidase labeled anti-salmonella antibody were added to a disposable test device. The mixture was incubated for 20 minutes at room temperature. Positive pressure was used to evacuate the fluid from the test device. The trapped material was washed three times by introduction of 200 µl of 0.01M phosphate buffered saline pH 7.2 containing 0.05% Tween 20 followed by evacuation of the fluid from the disposable test device using positive pressure. The disposable test device was placed in the luminometer and 100 µl of Lumiglo Chemiluminescent substrate (Kirkegarrd and Perry Laboratories, Gaithersburg, Md.) was added. The drawslide was immediately closed, and the light emission determined. The signal to noise ratio for a solution of *S. typhimurium* ($10^6$ organisms): *A. hydrophila* ($10^6$ organisms) was 1.83.

What is claimed is:

1. A method for determining the presence and quantity of an analyte on a surface comprising the steps of:
    a) collecting said analyte by wiping said surface with a disposable collection apparatus means, and
    b) adding collection fluid to said collection apparatus means,
    c) placing said collection fluid in a disposable test device with permeable filter means at its bottom end, an open top end, and transparent side walls;
    d) applying pressure to said disposable test device to force said fluid to pass through said permeable filter means and retaining said analyte on said permeable filter means,
    e) adding a reagent into said disposable test device thereby establishing a luminescent reaction in said test device;
    f) measuring the light emission resulting from said luminescent reaction with a photometer comprising a photodetector means and a light tight chamber for said disposable test device and a means to measure light passing through said transparent side wall of said test device;
    g) causing the said photometer means to output a signal indicative to the presence and amount of analyte.

2. A method according to claim 1 wherein steps (c) through (g) are performed in within 5 minutes.

3. A method according to claim 1 wherein disposable collection apparatus means is comprised of a soft absorbent.

4. A method according to claim 1 wherein disposable collection apparatus means consists of a spongy absorbent.

5. A method according to claim 1 wherein disposable collection apparatus means is comprised of a soft absorbent and a shaft.

6. A method according to claim 1 wherein collection fluid contains a detergent.

7. A method according to claim 1 wherein collection fluid contains a salt.

8. A method according to claim 1 wherein a washing fluid is added to said collection fluid in said disposable test device in step (c) and said wash solution is comprised of a salt solution containing detergents, and said wash solution lyses somatic cells and does not lyse microorganisms.

9. A method according to claim 1, and after performing step (d), the additional steps of adding a wash solution and applying pressure to said disposable test device, where said pressure forces said wash solution to pass through said filter means.

10. A method according to claim 1 wherein a bacteriolytic reagent is added to said disposable test device in step (e).

11. A method according to claim 1 wherein said analyte contains adenosine triphosphate (ATP) and said light emission correlates with the concentration of said ATP.

12. A method according to claim 1 wherein said luminescent reaction of step (e) is established by adding luciferin-luciferase.

13. A method according to claim 1 wherein the luminescent reaction is established by adding isoluminol.

14. A method according to claim 1 in which a large volume concentrating apparatus is used to concentrate the fluid in said disposable test device as part of step (c).

15. A method according to claim 1 in which said filter means is a hydrophilic permeable membrane.

16. A method according to claim 1 in which all light emitting substances are retained within disposable test device during the performance of step (f).

17. A method for determining the presence and quantity of an analyte on a surface comprising:
    a) collecting said analyte by wiping said surface with a disposable collection apparatus means, and
    b) adding collection fluid to said collection apparatus means,
    c) placing said collection fluid in a disposable test device with permeable filter means at its bottom end, an open top end, and transparent side walls;
    d) applying pressure to said disposable test device to force said fluid to pass through said permeable filter means and retaining said analyte on said permeable filter means,
    e) adding a detection reagent into said disposable test device, said detection reagent binding to said analyte;
    f) adding a wash solution to said disposable test device and applying pressure to said disposable test device to force said fluid to pass through said permeable filter means,
    g) establishing a luminescent reaction in said test device;
    h) measuring the light emission resulting from said luminescent reaction with a photometer comprising a photodetector means and a light tight chamber for said disposable test device and a means to measure light passing through said transparent side wall of said test device;
    i) causing the said photometer means to output a signal indicative to the presence and amount of analyte.

18. A method according to claim 17 wherein steps (c) through (i) are performed in within 30 minutes.

19. A method according to claim 17 wherein disposable collection apparatus means is comprised of a soft absorbent.

20. A method according to claim 17 wherein disposable collection apparatus means consists of a spongy absorbent.

21. A method according to claim 17 wherein disposable collection apparatus means is comprised of a soft absorbent and a shaft.

22. A method according to claim 17 wherein collection fluid contains a detergent.

23. A method according to claim 17 wherein collection fluid contains a salt.

24. A method according to claim 17 wherein a washing fluid is added to said collection fluid in said disposable test device in step (c) and said wash solution is comprised of a salt solution containing detergents.

25. A method according to claim 17 wherein particles coated with a specific antibody that binds said analyte are added to said disposable test device in step (c) with said collection fluid.

26. A method according to claim 17 wherein after performing step (d), the additional steps of adding a wash solution and applying pressure to said disposable test device, where said pressure forces said wash solution to pass through said filter means are performed.

27. A method according to claim 17 wherein said detection reagent is an enzyme conjugated to a binder, said binder is selected from the group consisting of antibodies, lectins, DNA fragments, and said binder binds to said analyte or analyte fragment and said enzyme is selected from the group consisting of peroxidases, phosphatases, oxidases, and luciferases.

28. A method according to claim 17 wherein said luminescent reaction of step (f) is established by addition of a chemiluminescent substrate.

29. A method according to claim 17 wherein step (d) is eliminated so that the said collection fluid and the said detection reagent are placed together into said disposable test device.

30. A method according to claim 17 in which a large volume concentrating apparatus is used to concentrate the fluid in said disposable test device as part of step (c).

* * * * *